US007621955B2

(12) United States Patent
Goble et al.

(10) Patent No.: US 7,621,955 B2
(45) Date of Patent: *Nov. 24, 2009

(54) FACET JOINT REPLACEMENT

(75) Inventors: E. Marlowe Goble, Logan, UT (US); T. Wade Fallin, Hyde Park, UT (US); Robert W. Hoy, Paradise, UT (US)

(73) Assignee: Facet Solutions, Inc., Hopkinton, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/734,488

(22) Filed: Apr. 12, 2007

(65) Prior Publication Data

US 2007/0185576 A1  Aug. 9, 2007

Related U.S. Application Data

(63) Continuation of application No. 11/219,099, filed on Sep. 1, 2005, which is a continuation of application No. 11/211,849, filed on Aug. 24, 2005, which is a continuation of application No. 10/421,078, filed on Apr. 23, 2003, now Pat. No. 7,041,136, which is a continuation of application No. 09/726,169, filed on Nov. 29, 2000, now Pat. No. 6,579,319.

(51) Int. Cl.
*A61F 2/44* (2006.01)
(52) U.S. Cl. .................................. 623/17.11
(58) Field of Classification Search ... 623/17.11–17.16; 606/246–247
See application file for complete search history.

(56) References Cited

U.S. PATENT DOCUMENTS

| 2,677,369 A | 5/1954 | Knowles |
| 3,247,000 A | 4/1966 | Taylor |
| 3,298,372 A | 1/1967 | Feinberg |

(Continued)

FOREIGN PATENT DOCUMENTS

CN    2386790 Y    7/2000

(Continued)

OTHER PUBLICATIONS

Shaw, M; Development of Artifical Facets- Biomechanical Perspective *51$^{st}$ Annual Metting of the Orthopaedic Research Society*, Poster No. 1263.

(Continued)

*Primary Examiner*—Thomas C Barrett
*Assistant Examiner*—Nicholas Woodall
(74) *Attorney, Agent, or Firm*—David W. Mlibas; Barbara Daniels; Daniel F. Justin

(57) ABSTRACT

A prosthesis for the replacement of a diseased or traumatized facet of a mammalian vertebra includes a surface that articulates with another prosthetic facet or a natural facet, a portion that replaces at least a bony portion of the diseased or traumatized spine facet which is to be replaced, and an element to attach the prosthesis to the vertebra in a manner that does not require attachment to or abutment against the posterior arch. A method of installing the prosthesis includes the steps of resecting at least a portion of a facet and attaching the prosthesis in a manner that does not require attachment or abutment against the posterior arch.

25 Claims, 17 Drawing Sheets

U.S. PATENT DOCUMENTS

| | | |
|---|---|---|
| 3,426,364 A | 2/1969 | Lumb |
| 3,486,505 A | 12/1969 | Morrison |
| 3,508,954 A | 4/1970 | White et al. |
| 3,648,691 A | 3/1972 | Lumb et al. |
| 3,857,642 A | 12/1974 | Miller |
| 3,867,728 A | 2/1975 | Stubstad et al. |
| 3,875,595 A | 4/1975 | Froning |
| 4,003,376 A | 1/1977 | McKay et al. |
| 4,092,078 A | 5/1978 | Klotz et al. |
| 4,289,123 A | 9/1981 | Dunn |
| 4,349,921 A | 9/1982 | Kuntz |
| 4,369,769 A | 1/1983 | Edwards |
| 4,479,491 A | 10/1984 | Martin |
| 4,483,334 A | 11/1984 | Murray |
| 4,501,269 A | 2/1985 | Bagby |
| 4,554,914 A | 11/1985 | Kapp et al. |
| 4,599,086 A | 7/1986 | Doty |
| 4,604,995 A | 8/1986 | Stephens et al. |
| 4,611,581 A | 9/1986 | Steffee |
| 4,641,636 A | 2/1987 | Cotrel |
| 4,653,481 A | 3/1987 | Howland et al. |
| 4,657,550 A | 4/1987 | Daher |
| 4,696,290 A | 9/1987 | Steffee |
| 4,743,260 A | 5/1988 | Burton |
| 4,759,769 A | 7/1988 | Hedman et al. |
| 4,772,287 A | 9/1988 | Ray et al. |
| 4,790,303 A | 12/1988 | Steffee |
| 4,800,874 A | 1/1989 | David et al. |
| 4,805,602 A | 2/1989 | Puno et al. |
| 4,827,918 A | 5/1989 | Olerud |
| 4,863,476 A | 9/1989 | Shepperd |
| 4,863,477 A | 9/1989 | Monson |
| 4,892,545 A | 1/1990 | Day et al. |
| 4,904,260 A | 2/1990 | Ray et al. |
| 4,911,718 A | 3/1990 | Lee et al. |
| 4,946,458 A | 8/1990 | Harms et al. |
| 4,955,908 A | 9/1990 | Frey et al. |
| 5,011,484 A | 4/1991 | Breard |
| 5,015,255 A | 5/1991 | Kuslich |
| 5,047,055 A | 9/1991 | Bao et al. |
| 5,071,437 A | 12/1991 | Steffee |
| 5,092,866 A | 3/1992 | Breard et al. |
| 5,092,867 A | 3/1992 | Harms et al. |
| 5,092,893 A | 3/1992 | Smith |
| 5,127,912 A | 7/1992 | Ray et al. |
| 5,129,900 A | 7/1992 | Asher et al. |
| 5,147,361 A | 9/1992 | Ojima et al. |
| 5,147,404 A | 9/1992 | Downey |
| 5,171,279 A | 12/1992 | Mathews |
| 5,171,280 A | 12/1992 | Baumgartner |
| 5,180,393 A | 1/1993 | Commarmond |
| 5,192,326 A | 3/1993 | Bao et al. |
| 5,236,460 A | 8/1993 | Barber |
| 5,246,458 A | 9/1993 | Graham |
| 5,258,031 A | 11/1993 | Salib et al. |
| 5,261,910 A | 11/1993 | Warden et al. |
| 5,263,953 A | 11/1993 | Bagby |
| 5,282,863 A | 2/1994 | Burton |
| 5,304,178 A | 4/1994 | Stahurski |
| 5,306,275 A | 4/1994 | Bryan |
| 5,306,308 A | 4/1994 | Gross et al. |
| 5,306,309 A | 4/1994 | Wagner et al. |
| 5,313,962 A | 5/1994 | Obenchain |
| 5,318,567 A | 6/1994 | Vichard |
| 5,360,430 A | 11/1994 | Lin |
| 5,366,455 A | 11/1994 | Dove et al. |
| 5,370,697 A | 12/1994 | Baumgartner |
| 5,375,823 A | 12/1994 | Navas |
| 5,387,213 A | 2/1995 | Breard et al. |
| 5,391,168 A | 2/1995 | Sanders et al. |
| 5,401,269 A | 3/1995 | Buttner-Janz et al. |
| 5,415,661 A | 5/1995 | Holmes |
| 5,437,669 A | 8/1995 | Yuan et al. |
| 5,437,672 A | 8/1995 | Alleyne |
| 5,439,464 A | 8/1995 | Shapiro |
| 5,443,516 A | 8/1995 | Albrektsson et al. |
| 5,456,722 A | 10/1995 | McLeod et al. |
| 5,458,641 A | 10/1995 | Ramirez Jimenez |
| 5,458,642 A | 10/1995 | Beer et al. |
| 5,458,643 A | 10/1995 | Oka et al. |
| 5,464,439 A | 11/1995 | Gendler |
| 5,470,333 A | 11/1995 | Ray |
| 5,476,463 A | 12/1995 | Boachie-Adjei et al. |
| 5,480,401 A | 1/1996 | Navas |
| 5,489,308 A | 2/1996 | Kuslich et al. |
| 5,496,318 A | 3/1996 | Howland et al. |
| 5,507,745 A | 4/1996 | Logroscino et al. |
| 5,507,813 A | 4/1996 | Dowd et al. |
| 5,514,180 A | 5/1996 | Heggeness et al. |
| 5,522,899 A | 6/1996 | Michelson |
| 5,527,312 A | 6/1996 | Ray |
| 5,531,745 A | 7/1996 | Ray |
| 5,531,747 A | 7/1996 | Ray |
| 5,534,028 A | 7/1996 | Bao et al. |
| 5,534,030 A | 7/1996 | Navarro et al. |
| 5,534,031 A | 7/1996 | Matsuzaki et al. |
| 5,540,688 A | 7/1996 | Navas |
| 5,545,166 A | 8/1996 | Howland |
| 5,545,229 A | 8/1996 | Parsons et al. |
| 5,549,607 A | 8/1996 | Olson et al. |
| 5,556,431 A | 9/1996 | Buttner-Janz |
| 5,556,687 A | 9/1996 | McMillin |
| 5,562,735 A | 10/1996 | Margulies |
| 5,562,736 A | 10/1996 | Ray et al. |
| 5,562,737 A | 10/1996 | Graf |
| 5,571,189 A | 11/1996 | Kuslich |
| 5,571,191 A * | 11/1996 | Fitz ........................ 623/17.11 |
| 5,572,191 A | 11/1996 | Lundberg |
| 5,582,612 A | 12/1996 | Lin |
| 5,584,832 A | 12/1996 | Schlapfer |
| 5,603,713 A | 2/1997 | Aust et al. |
| 5,609,634 A | 3/1997 | Voydeville |
| 5,645,597 A | 7/1997 | Krapiva |
| 5,645,599 A | 7/1997 | Samani |
| 5,649,926 A | 7/1997 | Howland |
| 5,653,762 A | 8/1997 | Pisharodi |
| 5,666,243 A | 9/1997 | Brent |
| 5,672,175 A | 9/1997 | Martin |
| 5,674,295 A | 10/1997 | Ray et al. |
| 5,674,296 A | 10/1997 | Bryan |
| 5,676,701 A | 10/1997 | Yuan et al. |
| 5,681,310 A | 10/1997 | Yuan et al. |
| 5,683,464 A | 11/1997 | Wagner et al. |
| 5,683,465 A | 11/1997 | Shinn et al. |
| 5,688,272 A | 11/1997 | Montague et al. |
| 5,690,629 A | 11/1997 | Asher et al. |
| 5,702,392 A | 12/1997 | Wu et al. |
| 5,702,450 A | 12/1997 | Bisserie |
| 5,702,453 A | 12/1997 | Rabbe et al. |
| 5,704,936 A | 1/1998 | Mazel |
| 5,713,900 A | 2/1998 | Benzel et al. |
| 5,716,415 A | 2/1998 | Steffee |
| 5,725,582 A | 3/1998 | Bevan et al. |
| 5,728,097 A | 3/1998 | Mathews |
| 5,735,899 A | 4/1998 | Schwartz et al. |
| 5,749,873 A | 5/1998 | Fairley |
| 5,755,796 A | 5/1998 | Ibo et al. |
| 5,772,661 A | 6/1998 | Michelson |
| 5,797,909 A | 8/1998 | Michelson |
| 5,814,046 A | 9/1998 | Hopf |
| 5,824,093 A | 10/1998 | Ray et al. |
| 5,824,094 A | 10/1998 | Serhan et al. |
| 5,836,948 A | 11/1998 | Zucherman et al. |
| 5,860,977 A | 1/1999 | Zucherman et al. |

| | | |
|---|---|---|
| 5,865,846 A | 2/1999 | Bryan et al. |
| 5,868,745 A | 2/1999 | Alleyne |
| 5,876,404 A | 3/1999 | Zucherman et al. |
| 5,888,223 A | 3/1999 | Bray, Jr. |
| 5,893,889 A | 4/1999 | Harrington |
| RE36,221 E | 6/1999 | Breard et al. |
| 5,916,267 A | 6/1999 | Tienboon |
| 5,951,555 A | 9/1999 | Rehak et al. |
| 5,961,516 A | 10/1999 | Graf |
| 5,986,169 A | 11/1999 | Gjunter |
| 6,001,130 A | 12/1999 | Bryan et al. |
| 6,004,322 A | 12/1999 | Bernstein |
| 6,014,588 A | 1/2000 | Fitz |
| 6,019,759 A | 2/2000 | Rogozinski |
| 6,019,792 A | 2/2000 | Cauthen |
| 6,039,761 A | 3/2000 | Li et al. |
| 6,039,763 A | 3/2000 | Shelokov |
| 6,048,342 A | 4/2000 | Zucherman et al. |
| 6,063,088 A | 5/2000 | Winslow |
| 6,063,121 A | 5/2000 | Xavier et al. |
| 6,066,325 A | 5/2000 | Wallace et al. |
| 6,068,630 A | 5/2000 | Zucherman et al. |
| RE36,758 E | 6/2000 | Fitz |
| 6,074,390 A | 6/2000 | Zucherman et al. |
| 6,080,157 A | 6/2000 | Cathro et al. |
| 6,090,112 A | 7/2000 | Zucherman et al. |
| 6,093,205 A | 7/2000 | McLeod et al. |
| 6,113,637 A | 9/2000 | Gill et al. |
| 6,132,464 A | 10/2000 | Martin |
| 6,132,465 A | 10/2000 | Ray et al. |
| 6,146,421 A | 11/2000 | Gordon et al. |
| 6,149,652 A | 11/2000 | Zucherman et al. |
| 6,151,934 A | 11/2000 | Chong et al. |
| 6,152,926 A | 11/2000 | Zucherman et al. |
| 6,156,038 A | 12/2000 | Zucherman et al. |
| 6,156,067 A | 12/2000 | Bryan et al. |
| 6,176,861 B1 | 1/2001 | Bernstein et al. |
| 6,179,838 B1 | 1/2001 | Fiz |
| 6,183,471 B1 | 2/2001 | Zucherman et al. |
| 6,190,387 B1 | 2/2001 | Zucherman et al. |
| 6,190,414 B1 | 2/2001 | Young et al. |
| 6,206,882 B1 | 3/2001 | Cohen |
| 6,206,922 B1 | 3/2001 | Zdeblick et al. |
| 6,228,118 B1 | 5/2001 | Gordon |
| 6,235,030 B1 | 5/2001 | Zucherman et al. |
| 6,238,397 B1 | 5/2001 | Zucherman et al. |
| 6,241,730 B1 | 6/2001 | Alby |
| 6,264,655 B1 | 7/2001 | Pisharodi |
| 6,267,764 B1 | 7/2001 | Elberg |
| 6,280,444 B1 | 8/2001 | Zucherman et al. |
| 6,290,700 B1 | 9/2001 | Schmotzer |
| 6,293,949 B1 | 9/2001 | Justis et al. |
| 6,312,469 B1 | 11/2001 | Gielen et al. |
| 6,314,325 B1 | 11/2001 | Fitz |
| 6,332,882 B1 | 12/2001 | Zucherman et al. |
| 6,332,883 B1 | 12/2001 | Zucherman et al. |
| 6,379,355 B1 | 4/2002 | Zucherman et al. |
| 6,402,750 B1 | 6/2002 | Atkinson et al. |
| 6,413,259 B1 | 7/2002 | Lyons et al. |
| 6,419,676 B1 | 7/2002 | Zucherman et al. |
| 6,419,677 B2 | 7/2002 | Zucherman et al. |
| 6,419,703 B1 | 7/2002 | Fallin et al. |
| 6,440,169 B1 | 8/2002 | Elberg et al. |
| 6,447,546 B1 | 9/2002 | Bramlet et al. |
| 6,451,019 B1 | 9/2002 | Zucherman et al. |
| 6,451,020 B1 | 9/2002 | Zucherman et al. |
| 6,458,131 B1 | 10/2002 | Ray |
| 6,461,359 B1 | 10/2002 | Tribus et al. |
| 6,471,704 B2 | 10/2002 | Gertzbein et al. |
| 6,475,219 B1 | 11/2002 | Shelokov |
| 6,478,796 B2 | 11/2002 | Zucherman et al. |
| 6,481,440 B2 | 11/2002 | Gielen et al. |
| 6,485,518 B1 | 11/2002 | Cornwall et al. |
| 6,500,178 B2 | 12/2002 | Zucherman et al. |
| 6,514,256 B2 | 2/2003 | Zucherman et al. |
| 6,527,806 B2 | 3/2003 | Ralph et al. |
| 6,540,747 B1 | 4/2003 | Marino |
| 6,540,785 B1 | 4/2003 | Gill et al. |
| 6,565,605 B2 | 5/2003 | Goble et al. |
| 6,579,319 B2 | 6/2003 | Goble et al. |
| 6,582,433 B2 | 6/2003 | Yun |
| 6,585,769 B1 | 7/2003 | Muhanna et al. |
| 6,610,091 B1 * | 8/2003 | Reiley ..................... 623/17.11 |
| 6,616,669 B2 | 9/2003 | Ogilvie et al. |
| 6,626,909 B2 | 9/2003 | Chin |
| 6,626,944 B1 | 9/2003 | Taylor |
| 6,652,527 B2 | 11/2003 | Zucherman et al. |
| 6,652,534 B2 | 11/2003 | Zucherman et al. |
| 6,652,585 B2 | 11/2003 | Lange |
| 6,669,729 B2 | 12/2003 | Chin |
| 6,695,842 B2 | 2/2004 | Zucherman et al. |
| 6,699,246 B2 | 3/2004 | Zucherman et al. |
| 6,699,247 B2 | 3/2004 | Zucherman et al. |
| 6,733,534 B2 | 5/2004 | Sherman |
| 6,761,719 B2 | 7/2004 | Justis et al. |
| 6,761,720 B1 | 7/2004 | Senegas |
| 6,783,527 B2 | 8/2004 | Drewry et al. |
| 6,796,983 B1 | 9/2004 | Zucherman et al. |
| 6,811,567 B2 | 11/2004 | Reiley |
| 6,835,205 B2 | 12/2004 | Atkinson et al. |
| 6,835,207 B2 | 12/2004 | Zacouto et al. |
| 2001/0007073 A1 | 7/2001 | Zucherman et al. |
| 2001/0012938 A1 | 8/2001 | Zucherman et al. |
| 2001/0016743 A1 | 8/2001 | Zucherman et al. |
| 2001/0021850 A1 | 9/2001 | Zucherman et al. |
| 2001/0031965 A1 | 10/2001 | Zucherman et al. |
| 2001/0039452 A1 | 11/2001 | Zucherman et al. |
| 2002/0029039 A1 | 3/2002 | Zucherman et al. |
| 2002/0065557 A1 | 5/2002 | Goble et al. |
| 2002/0072800 A1 | 6/2002 | Goble et al. |
| 2002/0091446 A1 | 7/2002 | Zucherman et al. |
| 2002/0099384 A1 | 7/2002 | Scribner et al. |
| 2002/0116000 A1 | 8/2002 | Zucherman et al. |
| 2002/0123806 A1 | 9/2002 | Reiley |
| 2002/0143331 A1 | 10/2002 | Zucherman et al. |
| 2002/0151895 A1 | 10/2002 | Soboleski et al. |
| 2002/0183746 A1 | 12/2002 | Zucherman et al. |
| 2003/0004572 A1 | 1/2003 | Goble et al. |
| 2003/0009226 A1 | 1/2003 | Graf |
| 2003/0028250 A1 | 2/2003 | Reiley et al. |
| 2003/0040797 A1 | 2/2003 | Fallin et al. |
| 2003/0055427 A1 | 3/2003 | Graf |
| 2003/0065330 A1 | 4/2003 | Zucherman et al. |
| 2003/0109880 A1 | 6/2003 | Shirado et al. |
| 2003/0153912 A1 | 8/2003 | Graf |
| 2003/0191470 A1 | 10/2003 | Ritland |
| 2003/0220642 A1 | 11/2003 | Freudiger |
| 2003/0220643 A1 | 11/2003 | Ferree |
| 2004/0006341 A1 | 1/2004 | Shaolian et al. |
| 2004/0006391 A1 | 1/2004 | Reiley |
| 2004/0024458 A1 | 2/2004 | Senegas et al. |
| 2004/0049189 A1 | 3/2004 | Le Couedic et al. |
| 2004/0049190 A1 | 3/2004 | Biedermann et al. |
| 2004/0049272 A1 | 3/2004 | Reiley |
| 2004/0049273 A1 | 3/2004 | Reiley |
| 2004/0049274 A1 | 3/2004 | Reiley |
| 2004/0049275 A1 | 3/2004 | Reiley |
| 2004/0049276 A1 | 3/2004 | Reiley |
| 2004/0049277 A1 | 3/2004 | Reiley |
| 2004/0049278 A1 | 3/2004 | Reiley |
| 2004/0049281 A1 | 3/2004 | Reiley |
| 2004/0073215 A1 | 4/2004 | Carli |
| 2004/0078082 A1 | 4/2004 | Lange |
| 2004/0082954 A1 | 4/2004 | Teitelbaum et al. |
| 2004/0087950 A1 | 5/2004 | Teitelbaum |
| 2004/0106995 A1 | 6/2004 | Le Couedic et al. |

| | | | |
|---|---|---|---|
| 2004/0111154 A1 | 6/2004 | Reiley | |
| 2004/0116927 A1 | 6/2004 | Graf | |
| 2004/0117017 A1 | 6/2004 | Pasquet et al. | |
| 2004/0127989 A1 | 7/2004 | Dooris et al. | |
| 2004/0143264 A1 | 7/2004 | Mcafee | |
| 2004/0147928 A1 | 7/2004 | Landry et al. | |
| 2004/0153071 A1 | 8/2004 | Zucherman et al. | |
| 2004/0158245 A1 | 8/2004 | Chin | |
| 2004/0167520 A1 | 8/2004 | Zucherman et al. | |
| 2004/0172025 A1 | 9/2004 | Drewry et al. | |
| 2004/0181282 A1 | 9/2004 | Zucherman et al. | |
| 2004/0181285 A1 | 9/2004 | Simonson | |
| 2004/0186475 A1 | 9/2004 | Falahee | |
| 2004/0220568 A1 | 11/2004 | Zucherman et al. | |
| 2004/0225289 A1 | 11/2004 | Biedermann et al. | |
| 2004/0230192 A1 | 11/2004 | Graf | |
| 2004/0230201 A1 | 11/2004 | Yuan et al. | |
| 2004/0230304 A1 | 11/2004 | Yuan et al. | |
| 2004/0236327 A1 | 11/2004 | Paul et al. | |
| 2004/0236328 A1 | 11/2004 | Paul et al. | |
| 2004/0236329 A1 | 11/2004 | Panjabi | |
| 2004/0243239 A1 | 12/2004 | Taylor | |
| 2005/0010291 A1 | 1/2005 | Stinson et al. | |
| 2005/0010293 A1 | 1/2005 | Zucherman et al. | |
| 2005/0010298 A1 | 1/2005 | Zucherman et al. | |
| 2005/0027361 A1 | 2/2005 | Reiley | |
| 2005/0033434 A1 | 2/2005 | Berry | |
| 2005/0033439 A1 | 2/2005 | Gordon et al. | |
| 2005/0043797 A1 | 2/2005 | Lee | |
| 2005/0043799 A1 | 2/2005 | Reiley | |
| 2005/0113927 A1 | 5/2005 | Malek | |
| 2005/0119748 A1 | 6/2005 | Reiley et al. | |
| 2005/0131406 A1 | 6/2005 | Reiley et al. | |
| 2005/0137705 A1 | 6/2005 | Reiley | |
| 2005/0137706 A1 | 6/2005 | Reiley | |
| 2005/0143818 A1 | 6/2005 | Yuan et al. | |
| 2005/0149190 A1 | 7/2005 | Reiley | |
| 2005/0154467 A1 | 7/2005 | Peterman et al. | |

FOREIGN PATENT DOCUMENTS

| | | | |
|---|---|---|---|
| EP | 408489 A1 | 1/1991 | |
| EP | 322334 B1 | 2/1992 | |
| EP | 667127 A1 | 8/1995 | |
| EP | 767637 B1 | 11/1998 | |
| EP | 768843 B1 | 2/1999 | |
| EP | 669109 B1 | 5/1999 | |
| EP | 1239785 B1 | 9/2004 | |
| EP | 1343424 B1 | 9/2004 | |
| EP | 1399078 B1 | 12/2004 | |
| FR | 2721501 B1 | 8/1996 | |
| JP | 10179622 A2 | 7/1998 | |
| JP | 10277070 A2 | 10/1998 | |
| SU | 1468543 A1 | 3/1989 | |
| SU | 1517953 A1 | 10/1989 | |
| WO | WO8707827 A1 | 12/1987 | |
| WO | WO9421185 A1 | 9/1994 | |
| WO | WO9505783 A1 | 3/1995 | |
| WO | WO9505784 A1 | 3/1995 | |
| WO | WO9505785 A1 | 3/1995 | |
| WO | WO9505786 A1 | 3/1995 | |
| WO | WO9600049 A1 | 1/1996 | |
| WO | WO9822033 A1 | 5/1998 | |
| WO | WO9848707 A1 | 11/1998 | |
| WO | WO9848717 A1 | 11/1998 | |
| WO | WO9856301 A1 | 12/1998 | |
| WO | WO9905995 A1 | 2/1999 | |
| WO | WO9921500 A1 | 5/1999 | |
| WO | WO9921501 A1 | 5/1999 | |
| WO | WO9923963 A1 | 5/1999 | |
| WO | WO9965412 A1 | 12/1999 | |
| WO | WO9960957 C2 | 5/2000 | |
| WO | WO0038582 C2 | 7/2000 | |
| WO | WO0062684 A1 | 10/2000 | |
| WO | WO0130248 A1 | 5/2001 | |
| WO | WO0145576 A1 | 6/2001 | |
| WO | WO0149192 A1 | 7/2001 | |
| WO | WO0156489 A1 | 8/2001 | |
| WO | WO0164142 A1 | 9/2001 | |
| WO | WO0164144 A2 | 9/2001 | |
| WO | WO0191657 A1 | 12/2001 | |
| WO | WO0191658 A1 | 12/2001 | |
| WO | WO0197721 A2 | 12/2001 | |
| WO | WO0200124 A1 | 1/2002 | |
| WO | WO0203882 A2 | 1/2002 | |
| WO | WO0207621 A1 | 1/2002 | |
| WO | WO0207622 A1 | 1/2002 | |
| WO | WO0207623 A1 | 1/2002 | |
| WO | WO0213732 A2 | 2/2002 | |
| WO | WO0230336 A2 | 4/2002 | |
| WO | WO0234120 A2 | 5/2002 | |
| WO | WO0243603 A1 | 6/2002 | |
| WO | WO02067792 A2 | 9/2002 | |
| WO | WO02067793 A2 | 9/2002 | |
| WO | WO02089712 A2 | 11/2002 | |
| WO | WO02089712 A1 | 11/2002 | |
| WO | WO02102259 A2 | 12/2002 | |
| WO | WO03009737 A1 | 2/2003 | |
| WO | WO03011147 A1 | 2/2003 | |
| WO | WO03015646 A2 | 2/2003 | |
| WO | WO03045262 A2 | 6/2003 | |
| WO | WO03077806 A1 | 9/2003 | |
| WO | WO2004017817 A2 | 3/2004 | |
| WO | WO2004019762 A2 | 3/2004 | |
| WO | WO2004024010 A1 | 3/2004 | |
| WO | WO2004032794 A2 | 4/2004 | |
| WO | WO2004039239 A2 | 5/2004 | |
| WO | WO2004039243 A2 | 5/2004 | |
| WO | WO2004041066 A2 | 5/2004 | |
| WO | WO2004073533 A1 | 9/2004 | |
| WO | WO2004098423 A1 | 11/2004 | |
| WO | WO2004098452 A2 | 11/2004 | |
| WO | WO2004105577 A2 | 12/2004 | |
| WO | WO2004105580 A2 | 12/2004 | |
| WO | WO2005013864 A1 | 2/2005 | |
| WO | WO2005037149 | 4/2005 | |
| WO | WO2005044152 A1 | 5/2005 | |

OTHER PUBLICATIONS

Goh JC, et al., "Influence of PLIF cage size on lumbar spine stability", Spine, Jan. 2000 25:1, PubMed abstract.

Head WC, Wagner surface replacement arthroplasty of the hip. Analysis of fourteen failures in forty-one hips:, J Bone Joint Surg. [Am], Mar. 1981 63:3, PubMed Abstract.

Kotani Y, et al., "The effects of spinal fixation and destabilization on the biomechanical and histologic properties of spinal ligaments. An in vivo study.", Spine, Mar. 15, 1998 23:6, PubMed abstract.

Lemaire JP, et al., "Intervertebral Disc Prosthesis: Results and Prospects for the Year 2000", Clinical Orthopaedics and Related Research, PubMed abstract.

Nagata H, et al., "The effects of immobilization of long segments of the spine on the adjacent and distal facet force and lumbrosacral motion", Spine, Dec. 1993 18:16. PubMed abstract.

Nibu K, et al., Multidirectional stabilizing potential of BAK interbody spinal fusion system for anterior surgery, J Spinal Discord, Aug. 1997 10:4, PubMed abstract.

Tsantrizos A, et al., "Segmental stability and compressive strength of posterior lumbar interbody fusion implants", Spine, Aug. 1, 2000 25:15, PubMed abstract.

Archus Orthopedics; Total Facet Arthroplasty System (TFAS). Website; http:/www.archususa.com/product.html.

* cited by examiner

FACET JOINT REPLACEMENT

CROSS-REFERENCE TO RELATED APPLICATIONS

This application is a continuation of:

U.S. application Ser. No. 11/219,099, filed Sep. 01, 2005 and entitled FACET JOINT REPLACEMENT, Which is a continuation of:

U.S. application Ser. No. 11/211,849, filed Aug. 24, 2005 and entitled FACET JOINT REPLACEMENT, Which is a continuation of:

U.S. application Ser. No. 10/421,078, filed Apr. 23, 2003 and entitled FACET REPLACEMENT, which is now issued as U.S. Pat. No. 7,041,136, Which is a continuation of:

U.S. application Ser. No. 09/726,169, filed Nov. 29, 2000 and entitled FACET JOINT REPLACEMENT, which is now issued as U.S. Pat. No. 6,579,319.

The disclosures listed above are incorporated herein by reference.

BACKGROUND OF THE INVENTION

1. The Field of the Invention

The present invention relates to surgical devices and methods to replace a damaged, diseased, or otherwise painful spinal facet joint.

2. The Relevant Technology

Traumatic, inflammatory, metabolic, synovial, neoplastic, and degenerative disorders of the spine can produce debilitating pain that can have severe socioeconomic and psychological effects. One of the most common surgical interventions today is arthrodesis, or spine fusion, of one or more motion segments, with approximately 300,000 procedures performed annually in the United States. Clinical success varies considerably, depending upon technique and indications, and consideration must be given to the concomitant risks and complications. For example, it has been shown that spine fusion decreases function by limiting the range of motion for patients in flexion, extension, rotation, and lateral bending. Furthermore, it is believed that spine fusion creates increased stresses and, therefore, accelerated degeneration of adjacent non-fused motion segments. Additionally, pseudoarthrosis, as a result of an incomplete or ineffective fusion, may reduce or even eliminate pain relief for the patient. Finally, the fusion device, whether artificial or biological, may migrate out of the fusion site.

Recently, several attempts have been made to recreate the natural biomechanics of the spine by use of an artificial disc. Artificial discs provide for articulation between vertebral bodies to recreate the full range of motion allowed by the elastic properties of the natural intervertebral disc which directly connects two opposed vertebral bodies.

However, the artificial discs proposed to date do not fully address the mechanics of motion of the spinal column. In addition to the intervertebral disc, posterior elements called the facet joints help to support axial, torsional and shear loads that act on the spinal column. Furthermore, the facet joints are diarthroidal joints that provide both sliding articulation and load transmission features. The effects of their absence as a result of facetectomy is believed to produce significant decreases in the stiffness of the spinal column in all planes of motion: flexion and extension, lateral bending, and rotation. Furthermore, contraindications for artificial discs include arthritic facet joints, absent facet joints, severe facet joint tropism or otherwise deformed facet joints.

U.S. Pat. No. Re. 36,758 to Fitz discloses an artificial facet joint where the inferior facet, the mating superior facet, or both, are covered with a cap. The cap requires no preparation of the bone or articular surfaces; it covers and, therefore, preserves the bony and articular structure.

The capping of the facet has several potential disadvantages. If the facet joint is osteoarthritic, a cap will not remove the source of the pain. Additionally, at least in the case of surface replacements for osteoarthritis femoral heads, the capping of articular bone ends has proven to lead to clinical failure by means of mechanical loosening. The clinical failure is hypothesized to be a sequela of disrupting the periosteum and ligamentum teres femoris, both serving a nutrition delivery role to the femoral head, thereby leading to avascular necrosis of the bony support structure for the surface replacement. Another potential disadvantage is that in order to accommodate the wide variability in anatomical morphology of the facets, not only between individuals but also between levels within the spinal column, a very wide variety of sizes and shapes would be required.

U.S. Pat. No. 6,132,464 to Martin discloses a spinal facet joint prosthesis that is supported on the lamina, or the posterior arch of the vertebra. Extending from this support structure are inferior and/or superior blades that replace the cartilage at the facet joint. Like the Fitz design, the Martin prosthesis generally preserves existing bony structures and therefore does not address pathologies which affect the bone of the facets in addition to affecting the associated cartilage. Furthermore, the Martin invention requires a mating condition between the prosthesis and the lamina, or the posterior arch, that is a thin base of curved bone that carries all four facets and the spinous process. Since the posterior arch is a very complex and highly variable anatomic surface, it would be very difficult to design a prosthesis that provides reproducible positioning to correctly locate the cartilage-replacing blades for the facet joints.

Another approach to surgical intervention for spinal facets is provided in WO9848717A1 to Villaret. While Villaret teaches the replacement of spine facets, the replacement is interlocked in a manner to immobilize the joint.

Facet joint replacement in conjunction with artificial disc replacements represent a unique solution to recreating a fully functional motion segment that is compromised due to disease or trauma. Together, facet joint and disc replacement can eliminate all sources of pain, return full function and range of motion, and completely restore the natural biomechanics of the spinal column. Additionally, degenerative or traumatized facet joints may be replaced in the absence of disc replacement when the natural intervertebral disc is unaffected by the disease or trauma.

It would therefore be an improvement in the art to provide a vertebral facet replacement device and method that replaces a bony portion of the facets so as to remove the source of arthritic, traumatic, or other disease mediated pain.

SUMMARY OF THE INVENTION

It is an object of the invention to provide an artificial vertebral facet that replaces the cartilage and a portion of the bone of a facet.

It is a further object of the invention to provide a method for preparing a facet for the installation of an artificial vertebral facet.

It is another object to provide a method for replacing a spinal facet.

It is yet another object of the invention to provide a total vertebral facet joint replacement.

In the preferred embodiment, an inferior facet of a superior vertebra is resected at the base of the facet where it connects to the posterior arch. The fin of a prosthetic inferior facet is pressed into the interior bone space of the posterior arch. Alternatively, a tool, such as a broach or punch, may be used to first prepare a space for the fin within the posterior arch.

Alternatively, or in addition, a superior facet of an inferior vertebra that articulates with the inferior facet is resected at the base of the facet where it connects to the pedicle. The post of a prosthetic superior facet is pressed into the interior bone space of the pedicle. Alternatively, a tool, such as a broach or punch, may be used to first prepare a space for the post within the pedicle.

The post and the fin may be porous coated to promote bone ingrowth in order to achieve long term fixation. Acute fixation is provided by a press fit between the post or fin and the internal surface of the bone. The porous coating may carry osteoconductive agents, such as hydroxylapatite, calcium sulfate, or demineralized bone matrix. Alternatively, the porous coating may carry osteoinductive agents, such as bone morphogenic proteins, including rhBMP-2 and rhBMP-7.

Another embodiment of the present invention provides a flange extending from the prosthetic facet. The flange is oriented relative to the body of the prosthesis such that when the flange is placed against the pedicle and in a manner such that the planar surface of the flange is perpendicular to the axis of the pedicle interior bone canal, the articulating surface of the prosthesis will be properly positioned to match the articulating surface of the natural facet. The flange includes a hole for the passage of a fastener to securely attach the prosthesis to the pedicle. The fastener can be a screw, spike, tack, staple, or the like.

Because the present invention allows for the individual replacements of facets, only compromised facets need be replaced. For example, if only one facet is affected by disease or trauma, it can be resected and replaced with a facet prosthesis that articulates with an opposing natural facet.

The present invention has numerous advantages over the prior art. One advantage is that the quality of attachment of the prosthesis is improved. The present invention provides a precise and tight press fit into bones, as opposed to relying on prosthetic surfaces mating with highly complex and variable external surfaces of the vertebra, such as the posterior arch or facet. Another advantage is that the optional porous coating is placed into interior bone spaces where porous coatings have proven to achieve bone ingrowth for excellent long term fixation strength. This ability to achieve bone ingrowth is uncertain for the prior art devices that engage the external bone surfaces of the vertebra. Yet another advantage lies in the removal of the facet bone structure; where the facet bone is involved in the disease pathology or the trauma that compromised the articular or cartilaginous surface of the facet, resection provides a means for ensuring that all pain associated with the disease or trauma is removed and the true joint line is restored. With prior art devices, the bony structure of the facets was generally left intact.

The above, and other objects, features and advantages of the present invention, will become apparent from the following description which is to be read in conjunction with the accompanying drawings.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts and further wherein.

DETAILED DESCRIPTION OF THE PREFERRED EMBODIMENTS

Figure 1:
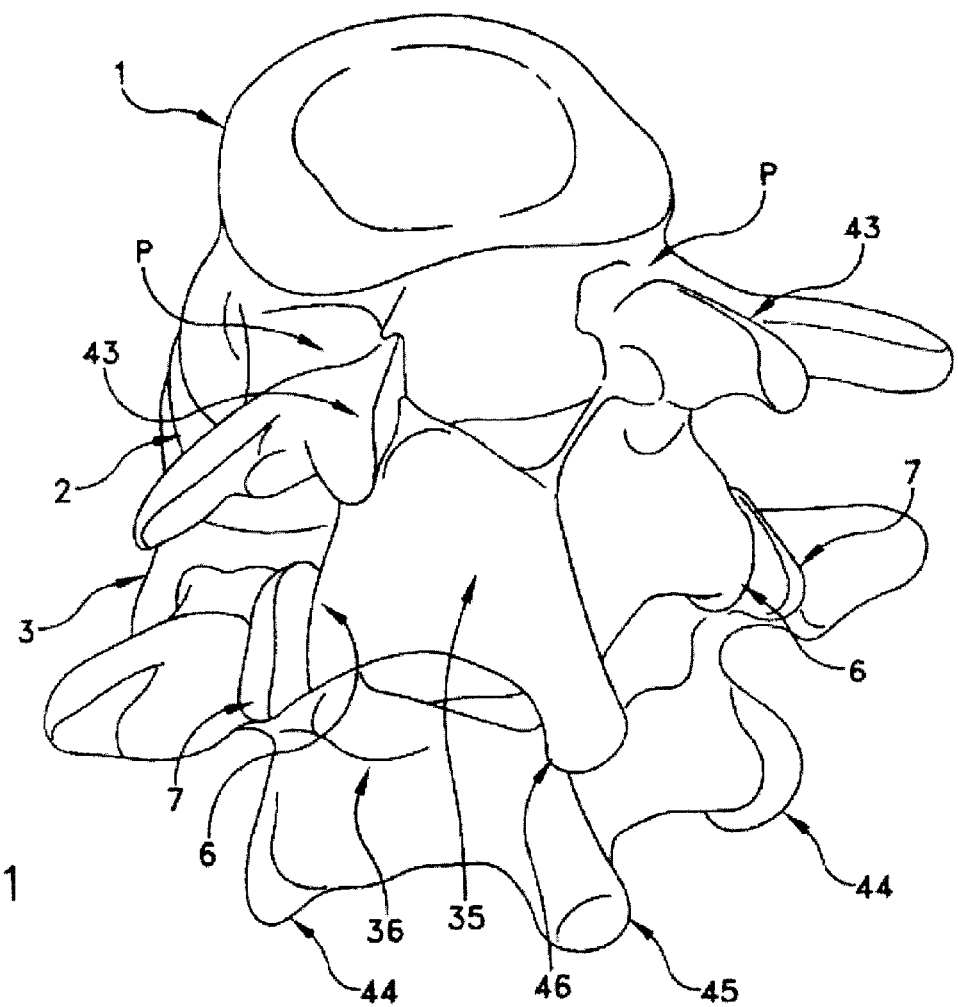
FIG. 1 is a perspective view of a portion of the spine.
Figure 1A:
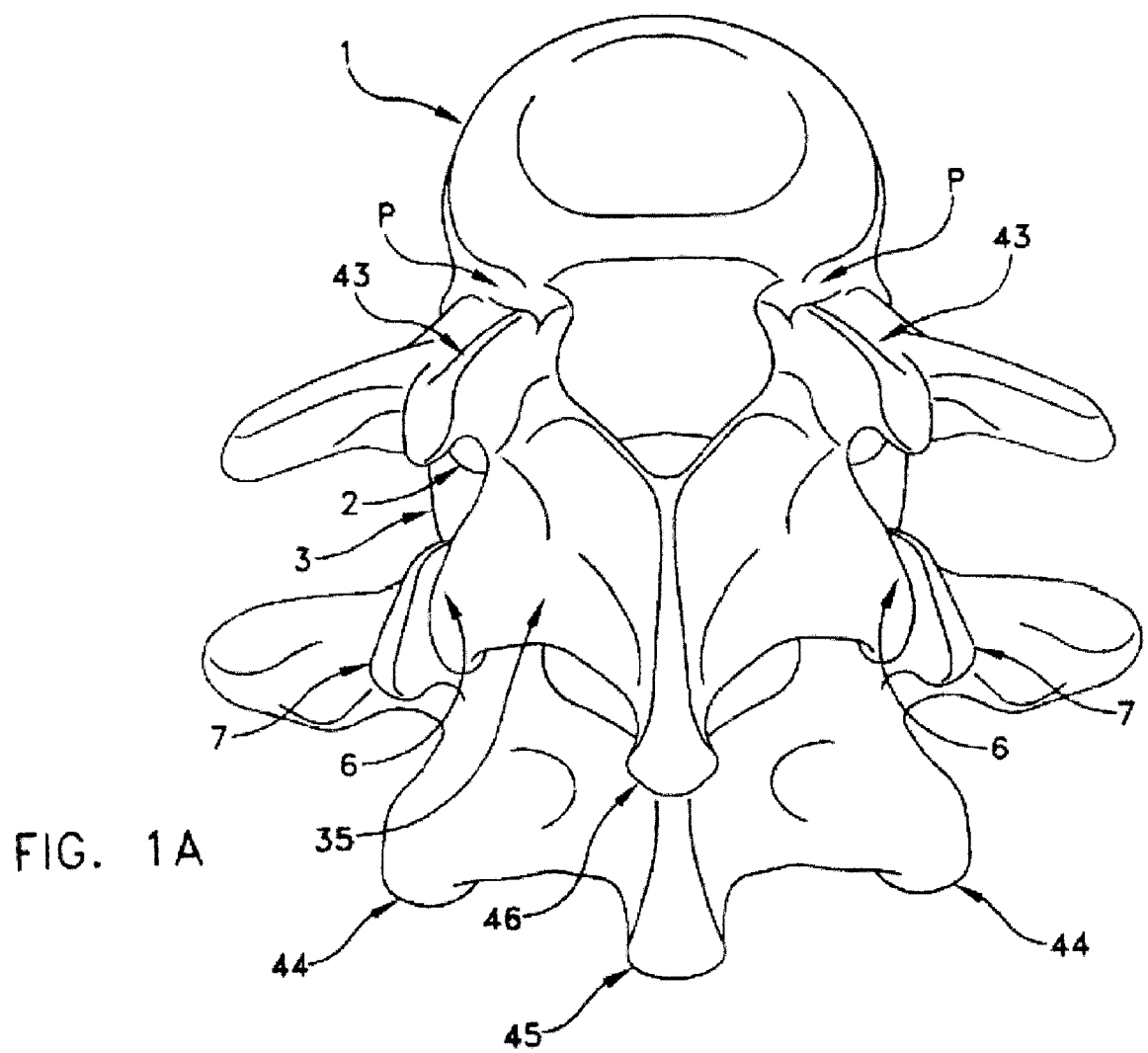
FIG. 1A is a dorsal view of the portion of the spine shown in FIG. 1.

Referring now to FIGS. 1 and 1A, there is shown a superior vertebra 1 and an inferior vertebra 3, with an intervertebral disc 2 located in between. Vertebra 1 has superior facets 43, inferior facets 6, posterior arch 35 and spinous process 46. Vertebra 3 has superior facets 7, inferior facets 44, posterior arch 36 and spinous process 45.

Figure 2:
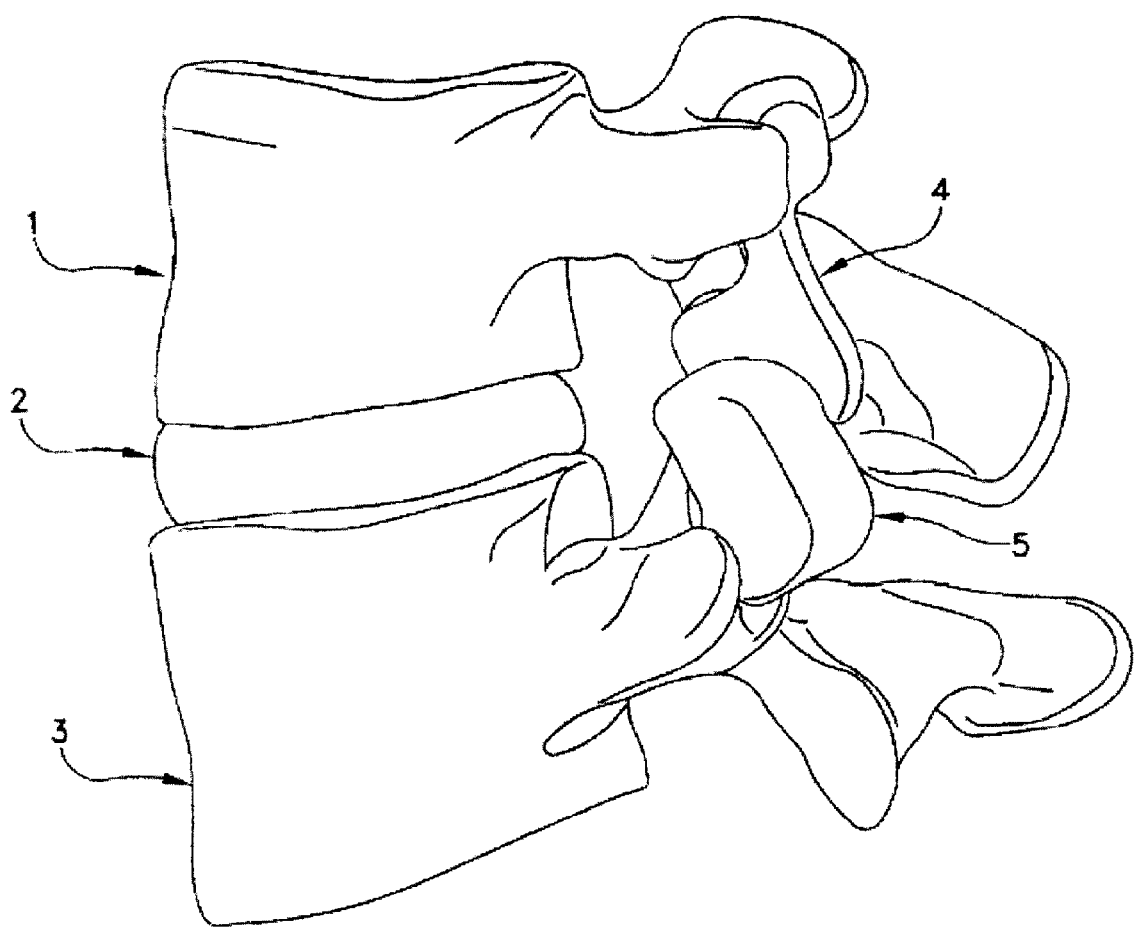
FIG. 2 is a lateral view of a facet joint reconstructed in accordance with the present invention.

Referring now to FIG. 2, the left inferior facet 6 of vertebra 1 has been resected and an inferior facet prosthesis 4 has been attached to vertebra 1. Similarly, the left superior facet of vertebra 3 has been resected and a superior facet prosthesis 5 has been attached to vertebra 3.

Figure 3:
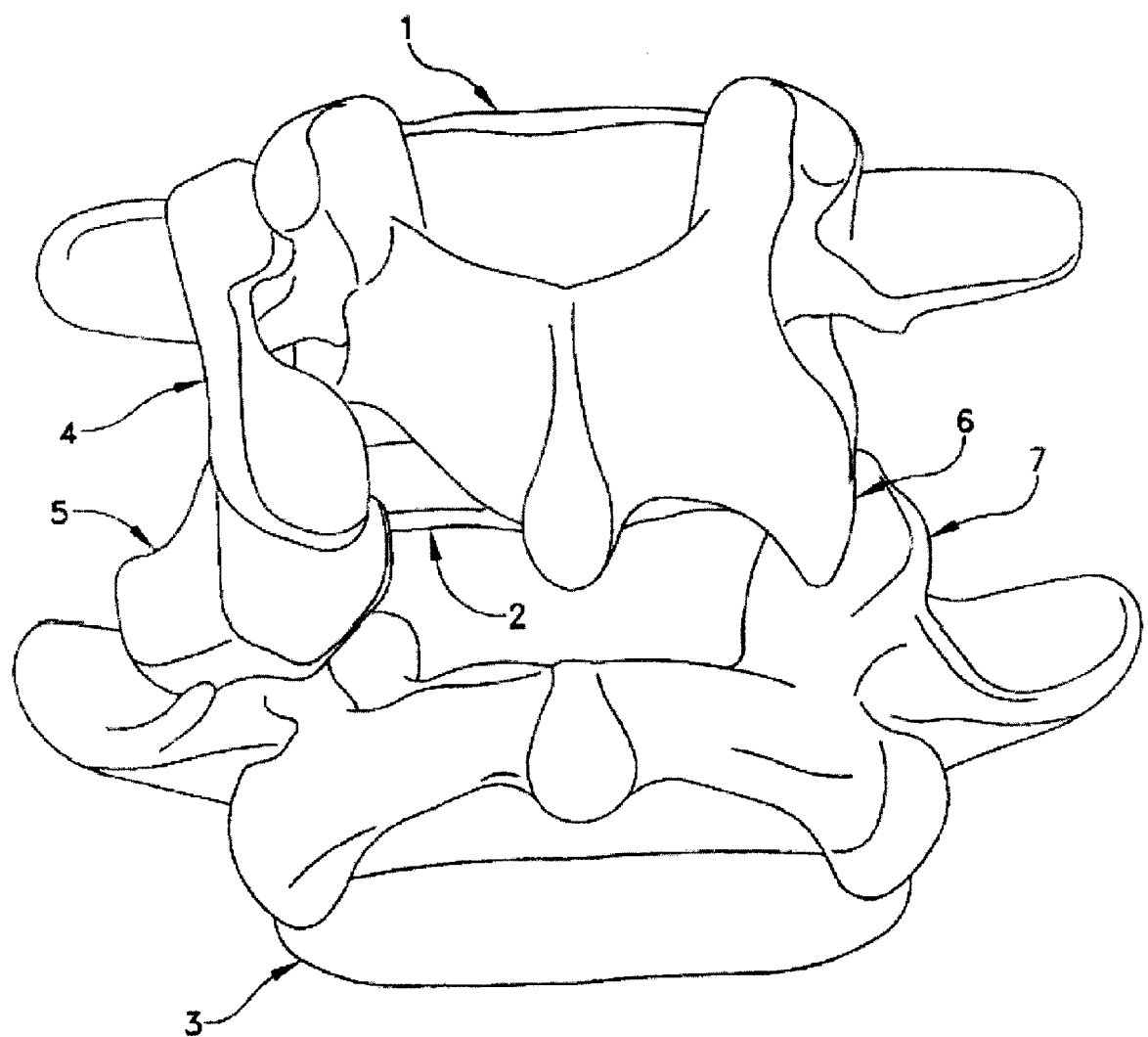
FIG. 3 is a dorsal view of the facet joint shown in FIG. 2.

FIG. 3 illustrates a dorsal view of the elements shown in 2. It can be appreciated that inferior facet prosthesis 4 replicates the natural anatomy when compared to the contralateral inferior facet 6 of vertebra 1. Similarly, it can be appreciated that superior facet prosthesis 5 replicates the natural anatomy when compared to the contralateral superior facet 7 of vertebra 3.

Figure 4:
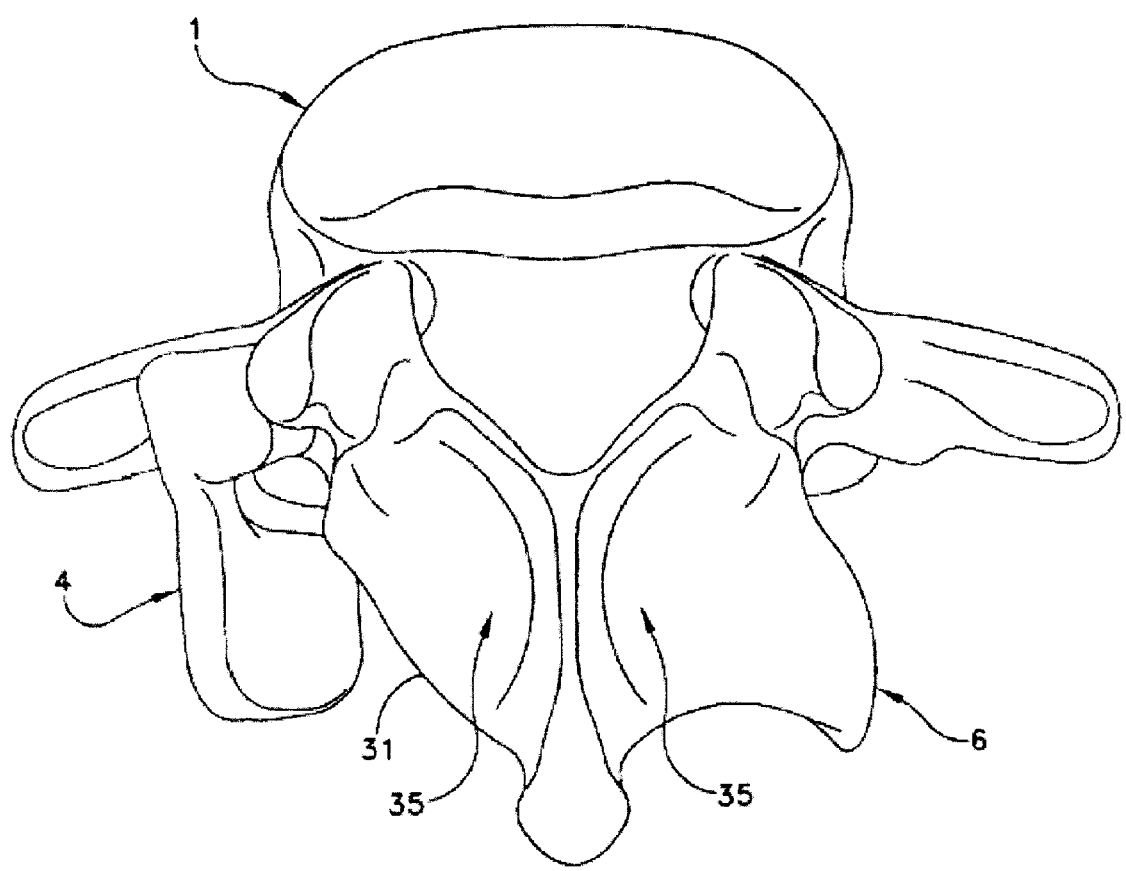
FIG. 4 is a perspective view of the implanted left inferior facet prosthesis shown in FIGS. 2 and 3.
Figure 5:
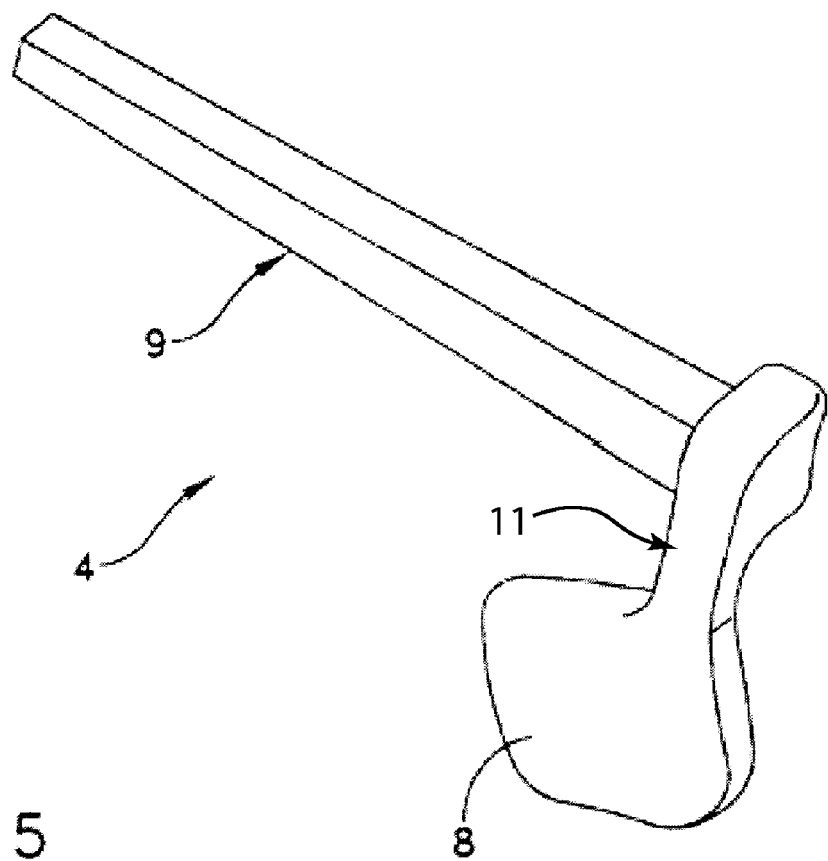
FIG. 5 is a perspective view of the left inferior facet prosthesis shown in FIGS. 2 and 3.

Turning now to FIG. 4, a perspective view of vertebra 1 with implanted inferior facet prosthesis 4 is provided. Resection at 31 has removed the natural inferior facet 6 at the bony junction between the inferior facet 6 and the posterior arch 35. In this manner, any bone pain associated with a disease, such as osteoarthritis, or trauma will be eliminated as the involved bony tissue has been osteotomized FIG. 5 illustrates a perspective view of inferior facet prosthesis 4. Surface 8 replicates the natural articular surface of the replaced inferior facet 6. Post 9 provides a means to affix inferior facet prosthesis 4 to vertebra 1. Strut 11 extends between surface 8 and post 9. Post 9 is implanted into the interior bone space of the left pedicle P (FIG. 6) on vertebra 1 and may or may not extend into the vertebral body of vertebra 1 to provide additional stability.

Figure 6:
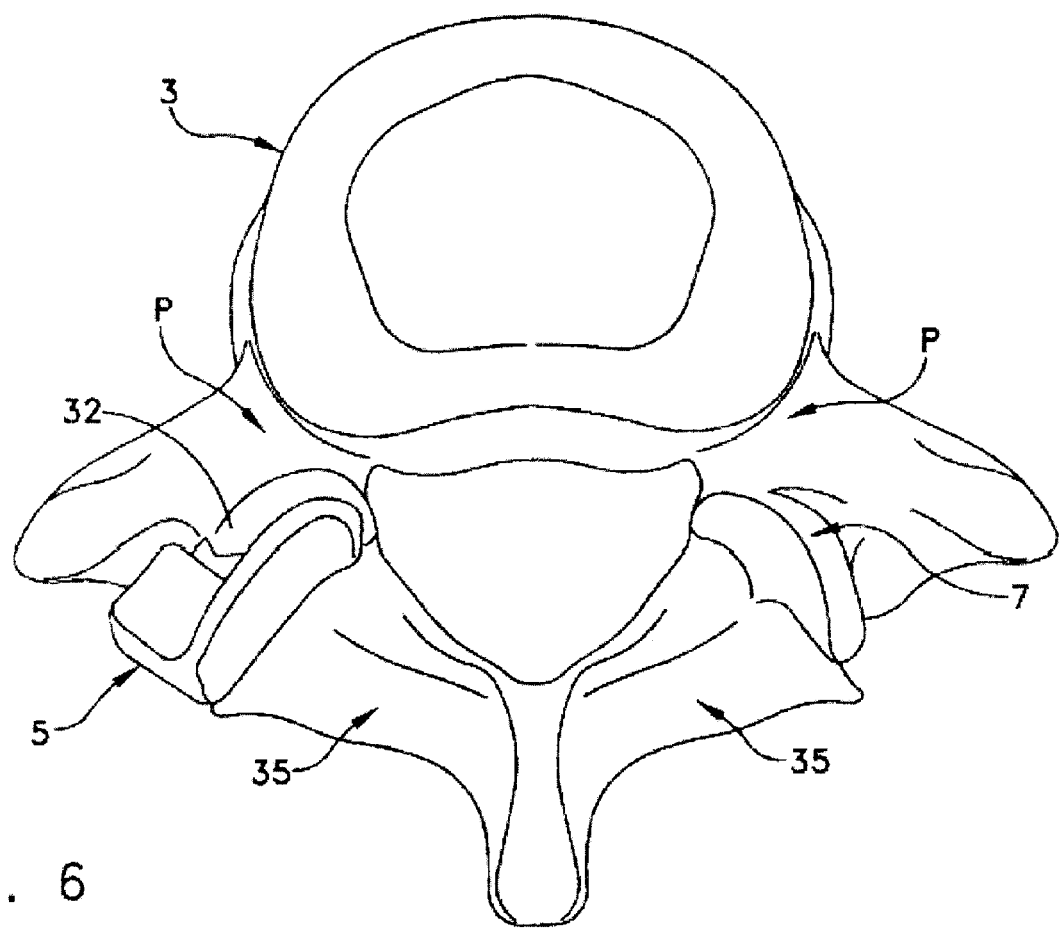
FIG. 6 is a cranial view of the implanted left superior facet prosthesis shown in FIGS. 2 and 3.

FIG. 6 illustrates a cranial view of vertebra 3 with implanted superior facet prosthesis 5. Resection surface 32 represents the bony junction between the natural superior facet and the posterior arch 35.

Figure 7:
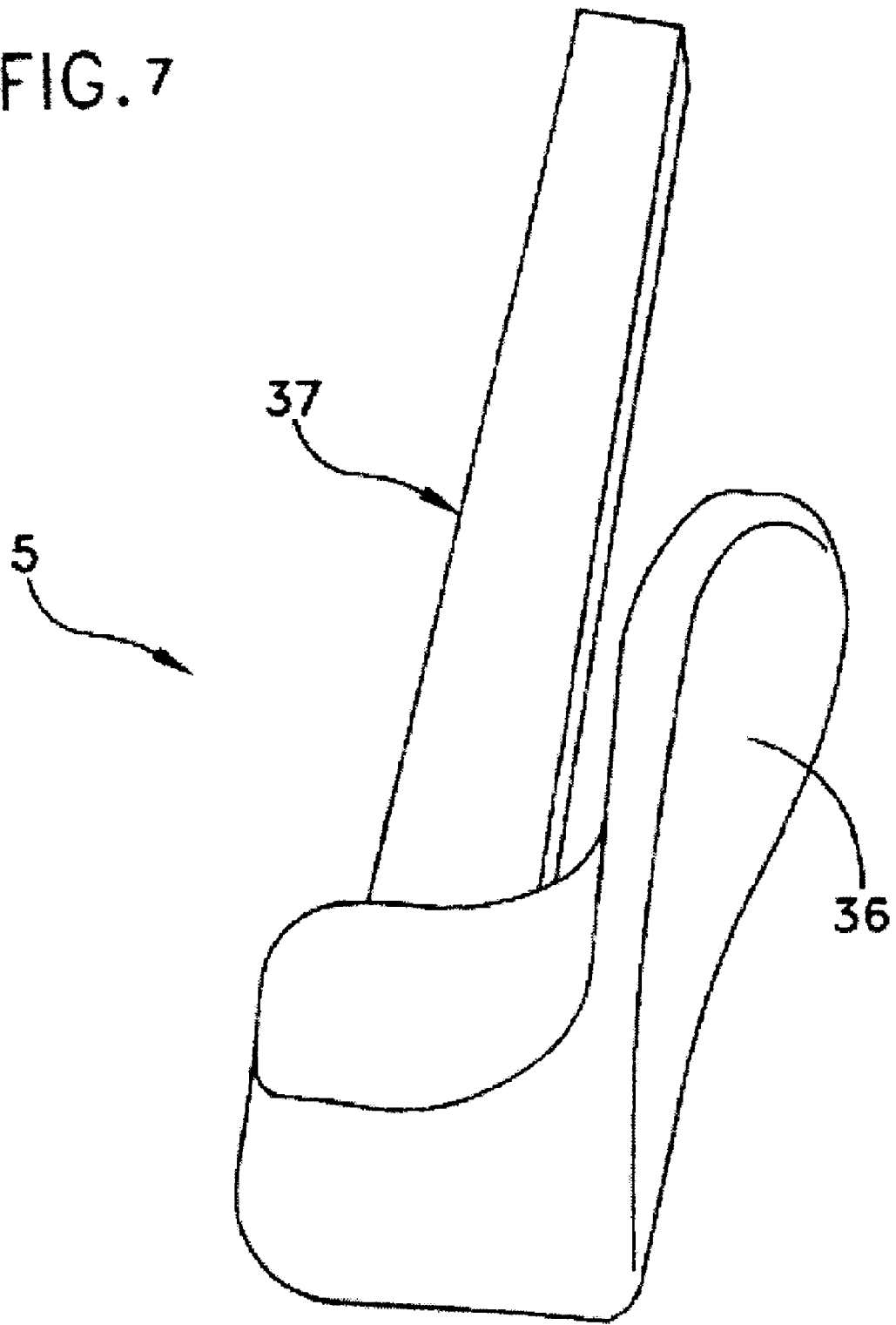
FIG. 7 is a perspective view of the left superior facet prosthesis shown in FIGS. 2 and 3.

FIG. 7 illustrates a perspective view of superior facet prosthesis 5. Surface 36 replicates the natural articular surface of the replaced superior facet 7. Post 37 provides a means for affixing superior facet prosthesis 5 to vertebra 3. Post 37 is implanted into the interior bone space of the left pedicle P (FIG. 6) on vertebra 3 and may or may not extend into the vertebral body of vertebra 3 to provide additional stability.

When the total facet joint is replaced, as shown in FIGS. 2 and 3, then surface 8 (FIG. 5) articulates with surface 36 (FIG. 7) to recreate the natural biomechanics of the spine motion segment made up of vertebra 1, vertebra 3, and intervertebral disc 2.

Figure 8:
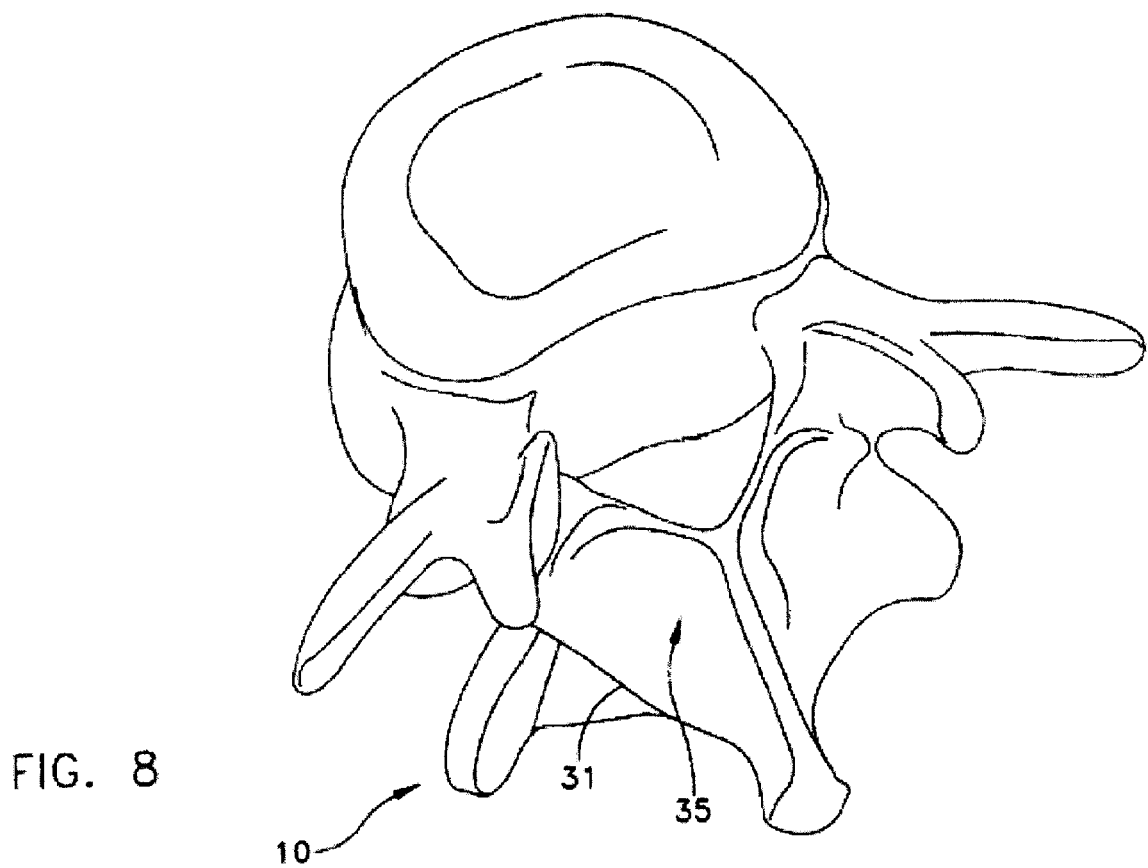
FIG. 8 is a perspective view of an alternate implanted left superior facet prosthesis.

FIG. 8 illustrates an alternative inferior facet prosthesis 10 which is implanted into the interior bone space of posterior arch 35. The interior bone space is accessed from the resection 31.

Figure 9:
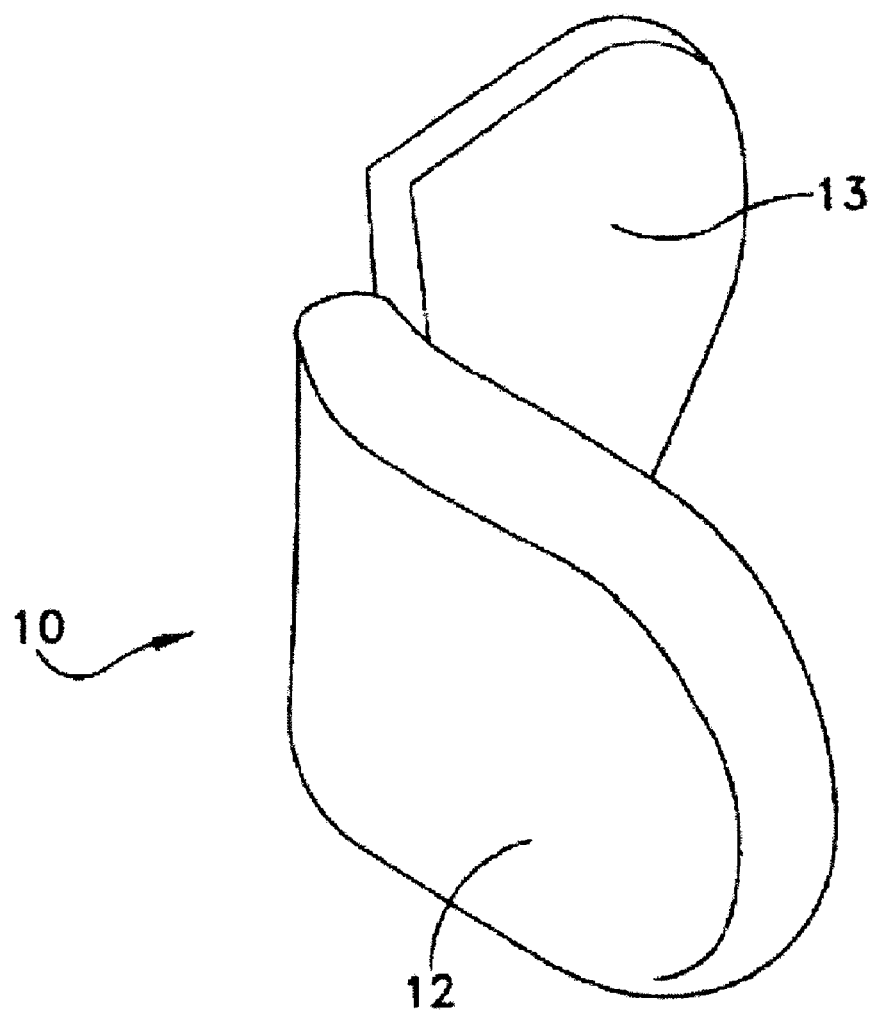
FIG. 9 is a perspective view of an alternate left superior facet prosthesis.

FIG. 9 shows details of alternative inferior facet prosthesis 10, including the fin 13 that extends into the interior bone space of posterior arch 35. Surface 12 replicates the natural articular surface of the replaced facet.

If desired, a corresponding fin construction can be used to form a prosthetic superior facet.

The surfaces of post 9 (FIG. 5), post 37 (FIG. 7) and fin 13 (FIG. 9) may or may not include porous coatings to facilitate bone ingrowth to enhance the long term fixation of the implant. Furthermore, such porous coatings may or may not include osteoinductive or osteoconductive substances to further enhance the bone remodeling into the porous coating.

Figure 10:
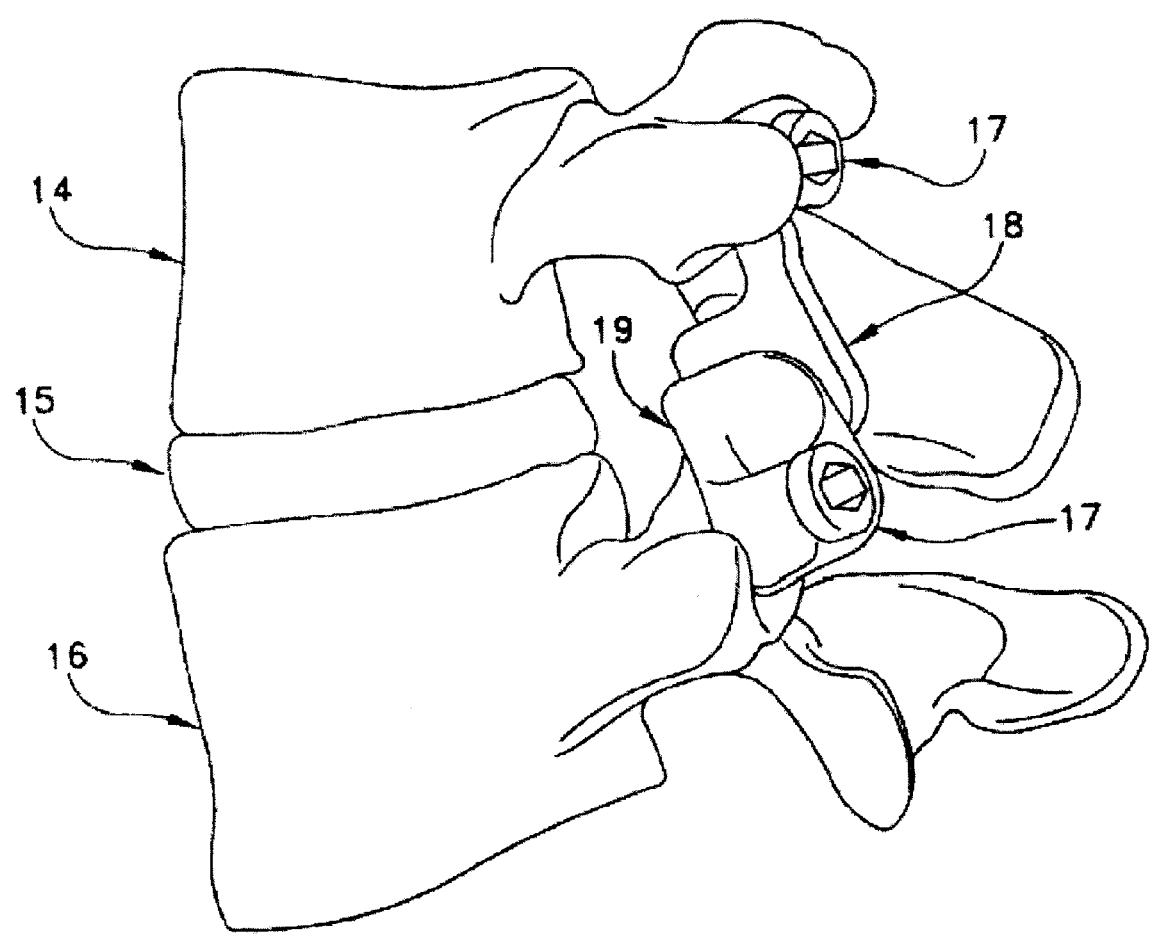
FIG. 10 is a lateral view of an alternative reconstructed facet joint.

Referring now to FIG. 10, there is shown a lateral view of a superior vertebra 14 and an inferior vertebra 16, with an intervertebral disc 15 located in between is shown. The left inferior facet of vertebra 14 has been resected and an inferior facet prosthesis 18 has been attached to vertebra 14 by means of a screw fastener 17, wherein the screw fastener is implanted into an interior bone space of the pedicle of the vertebra. Similarly, the left superior facet of vertebra 16 has been resected and a superior facet prosthesis 19 has been attached to vertebra 16 by means of a screw fastener 17, wherein the screw fastener is implanted into an interior bone space of the pedicle of the vertebra.

Figure 11:
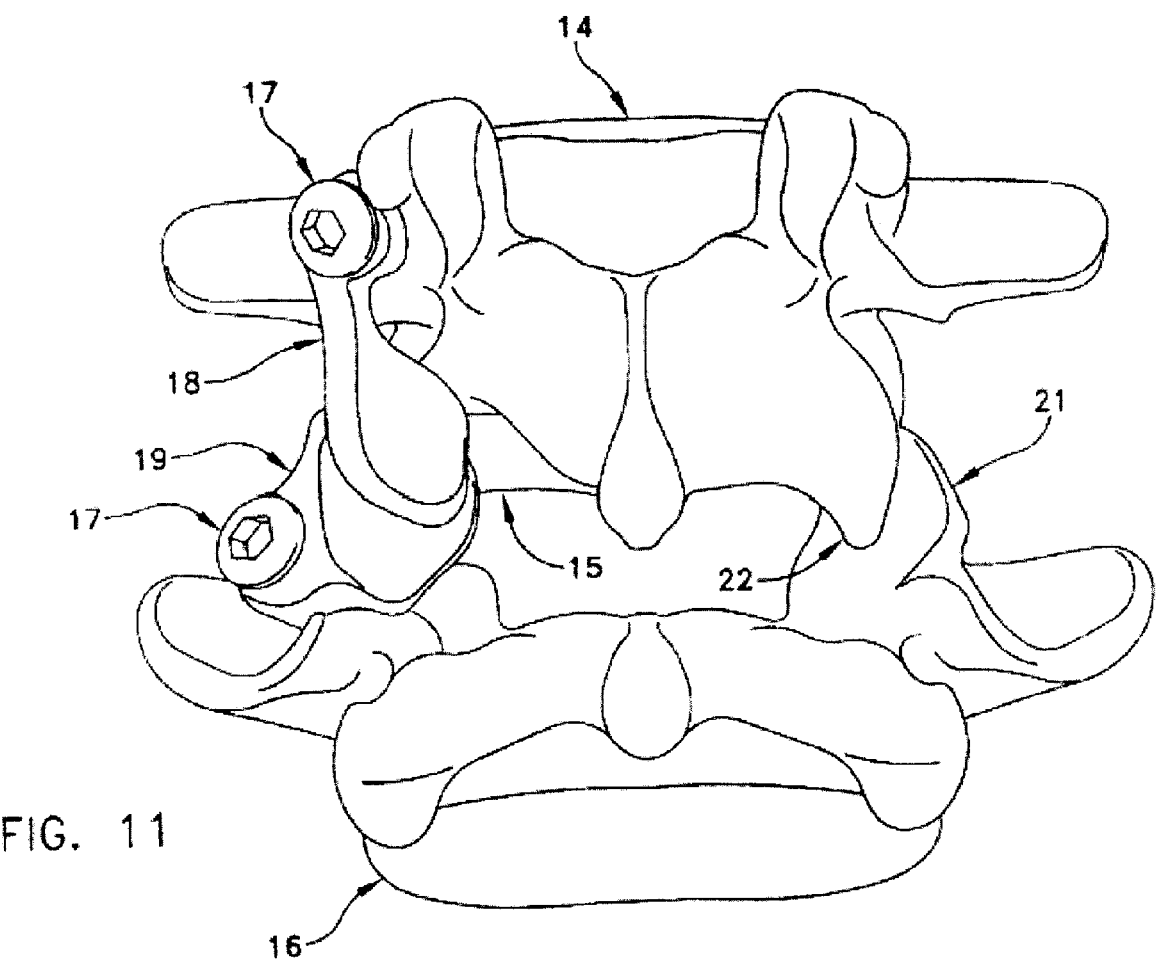
FIG. 11 is a dorsal view of an alternative reconstructed facet joint.

FIG. 11 illustrates a dorsal view of the elements of FIG. 10. It can be appreciated that inferior facet prosthesis 18 replicates the natural anatomy when compared to the contralateral inferior facet 22 of vertebra 14. Similarly, it can be appreciated that superior facet prosthesis 19 replicates the natural anatomy when compared to the contralateral superior facet 21 of vertebra 16. In a preferred embodiment of the present invention, inferior facet prosthesis 18 and/or superior facet prosthesis 19 has a bone contacting surface which is porous coated to allow for bone ingrowth.

Figure 12:
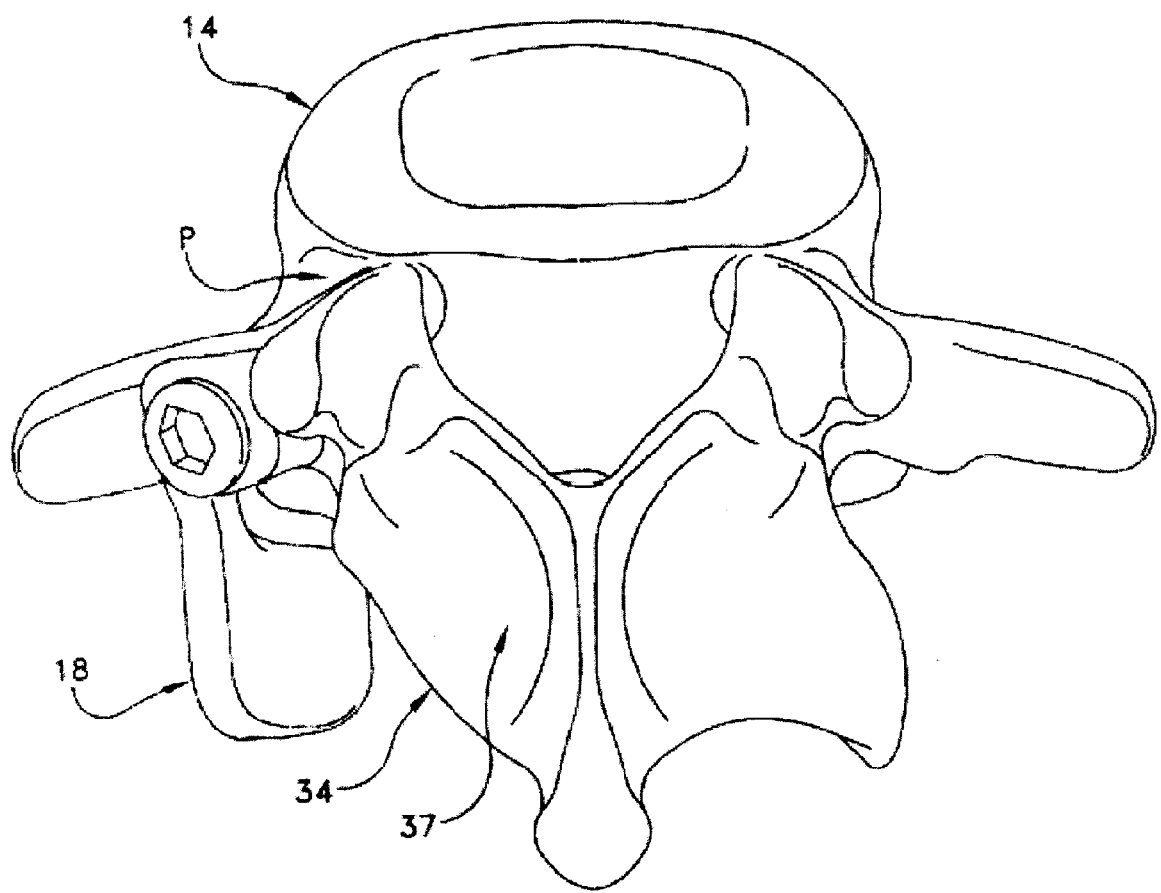
FIG. 12 is a perspective view of the implanted left inferior facet prosthesis shown in FIGS. 10 and 11.

Turning now to FIG. 12, there is provided a perspective view of vertebra 14 with implanted inferior facet prosthesis 18. Resection 34 has removed the natural inferior facet at the bony junction between the inferior facet and the posterior arch 37. In this manner, any bone pain associated with a disease, such as osteoarthritis, or trauma will be eliminated inasmuch as the involved bony tissue has been osteotomized.

Figure 13:
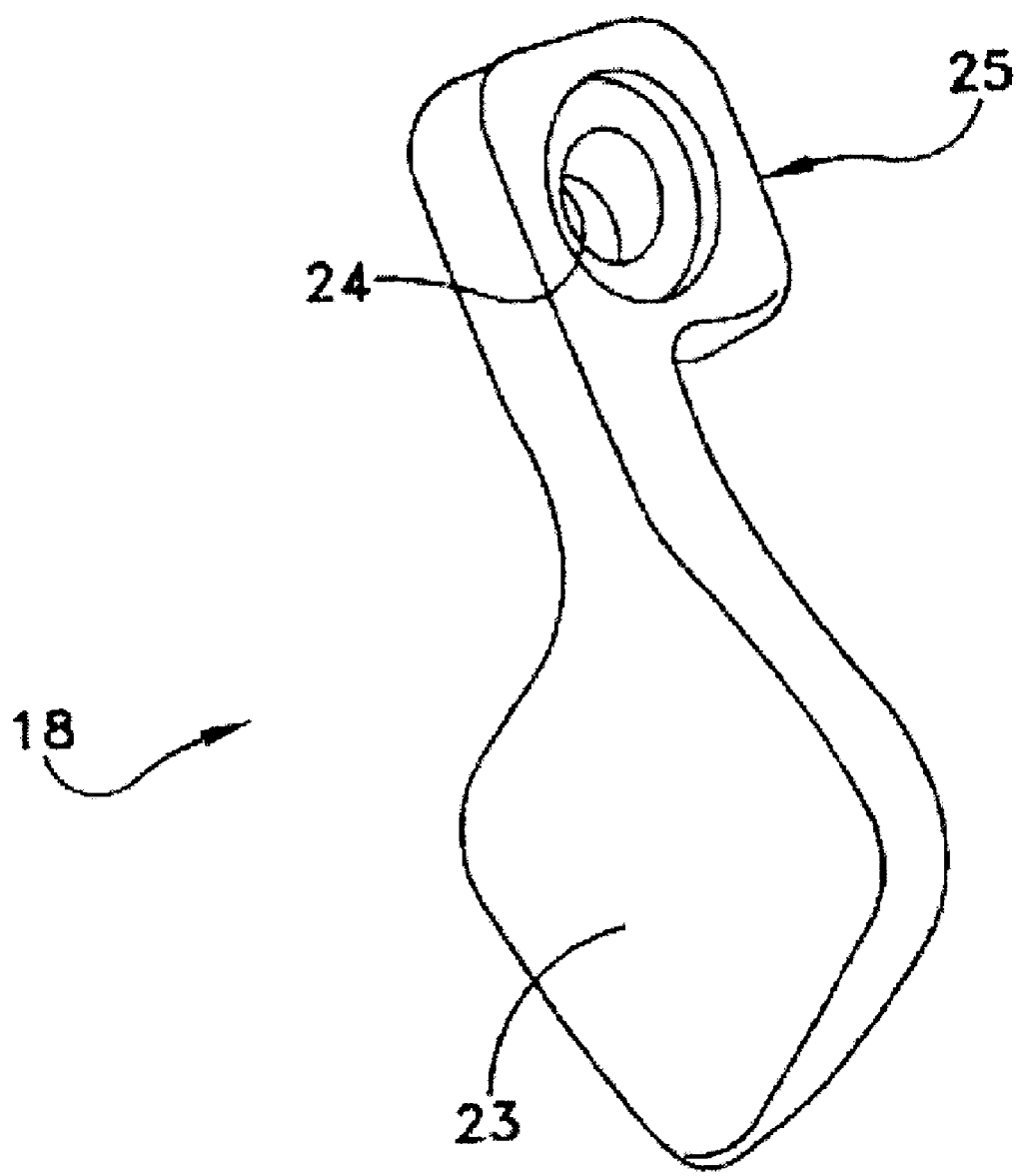
FIG. 13 is a perspective view of the alternative left inferior facet prosthesis shown in FIGS. 10 and 11.

FIG. 13 illustrates a perspective view of inferior facet prosthesis 18. Surface 23 replicates the natural articular surface of the replaced facet. Flange 25 contacts the pedicle and hole 24 receives a fastener to attach inferior facet prosthesis 18 to vertebra 14.

Figure 14:
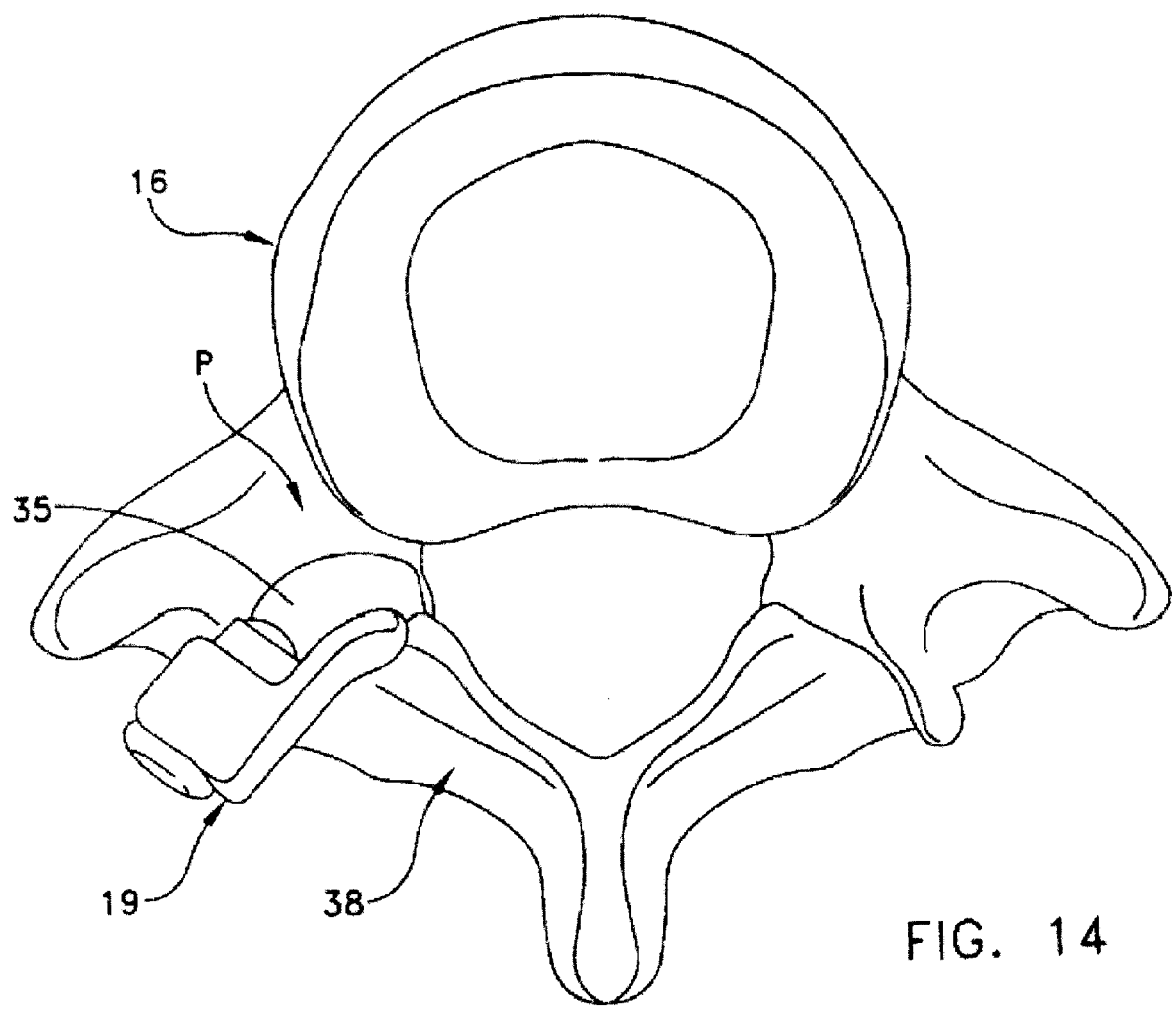
FIG. 14 is a cranial view of the alternative implanted left superior facet prosthesis shown in FIGS. 10 and 11

FIG. 14 illustrates a cranial view of vertebra 16 with implanted superior facet prosthesis 19. Resection surface 35 represents the bony junction between the natural superior facet and the posterior arch 38.

Figure 15:
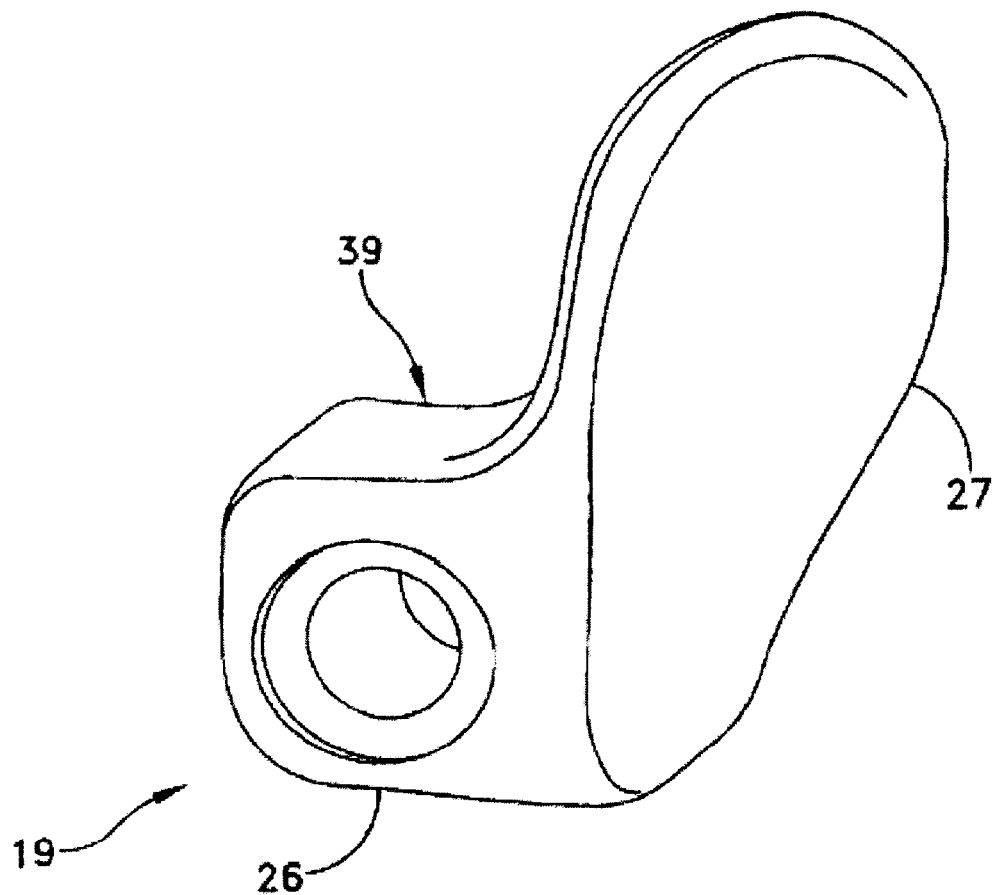
FIG. 15 is a perspective view of the alternative left superior facet prosthesis shown in FIGS. 10 and 11.

FIG. 15 illustrates a perspective view of superior facet prosthesis 19. Surface 27 replicates the natural articular surface of the replaced facet. Flange 39 contacts the pedicle and hole 26 receives a fastener to attach inferior facet prosthesis 19 to vertebra 16.

Figure 16:
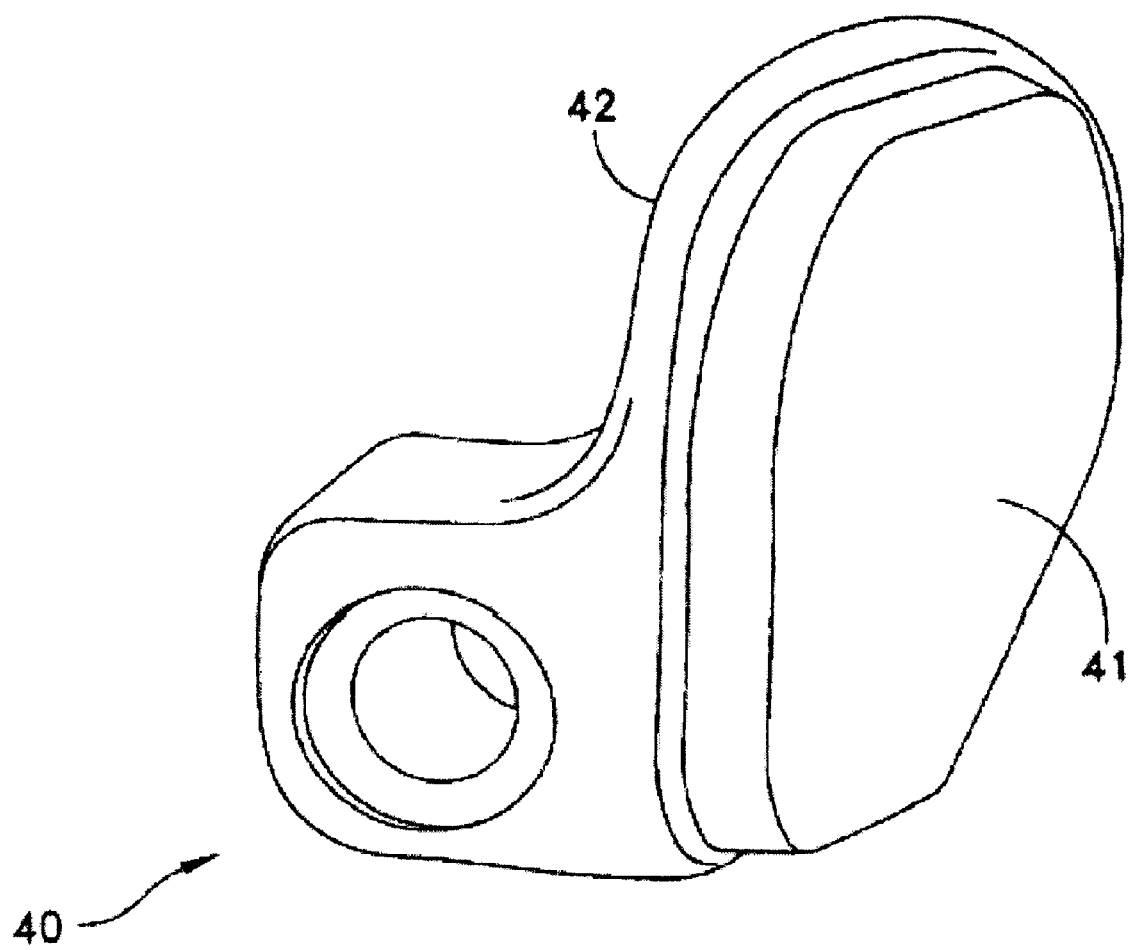
FIG. 16 is a perspective view of an alternate bearing surface for the superior facet prosthesis shown in FIG. 15.

FIG. 16 illustrates an alternative superior facet prosthesis 40 with an bearing surface 41 that mounts to substrate 42. The bearing surface 41 is a biocompatible polymeric material, such as ultra high molecular weight polyethylene. Alternately, the bearing surface can be ceramic, such as zirconia or alumina, or metal. The substrate is a biocompatible metal alloy, such as an alloy of titanium, cobalt, or iron.

Having described preferred embodiments of the invention with reference to the accompanying drawings, it is to be understood that the embodiments shown herein are by way of example, and that various changes and modifications may be effected by one skilled in the art without departing from the scope or spirit of the invention as defined in the following claims.

The invention claimed is:

1. A system for replacing at least a portion of a natural facet of a first vertebra, the system comprising:
   a first prosthesis comprising:
   a fixation member implantable in a pedicle of the first vertebra;
   a strut comprising a first end formed monolithically with the fixation member, and a second end extending from the first end along a direction transverse to a longitudinal axis of the fixation member, wherein the strut has a length extending between the first and second ends along the direction and a width perpendicular to the length; and
   a first articular surface on the second end, wherein the first articular surface is shaped to replace a natural articular surface of the first vertebra;
   wherein the strut is shaped to avoid encircling a spinous process of the first vertebra;
   wherein the strut width is narrower than the articular surface.

2. The system of claim 1, wherein the first articular surface is positioned on the strut independently of any other articular surface.

3. The system of claim 1, wherein the first articular surface is formed monolithically with the strut.

4. The system of claim 1, wherein the fixation member comprises a distal end configured to be retained in the pedicle independently of any threaded engagement.

5. The system of claim 1, wherein the first articular surface comprises an inferior articular surface.

6. The system of claim 1, wherein the first articular surface comprises a superior articular surface.

7. The system of claim 1, wherein the first prosthesis is configured to be securable to the first vertebra without resection of a lamina of the first vertebra, and without being supported by the lamina.

8. The system of claim 1, wherein the first prosthesis is configured to be securable to the first vertebra without requiring resection of any spinous process or transverse process of the first vertebra, and without requiring contact of the first prosthesis with any spinous process or transverse process of the first vertebra.

9. The system of claim 1, further comprising a second prosthesis securable to a second vertebra adjacent to the first vertebra, the second prosthesis comprising a second articular surface shaped to articulate with the first articular surface.

10. A system for replacing at least a portion of a natural facet of a first vertebra, the system comprising:
    a first prosthesis comprising:
    a fixation member implantable in a pedicle of the first vertebra;
    a strut comprising a first end formed monolithically with the fixation member, and a second end extending from the first end along a direction transverse to a longitudinal axis of the fixation member, wherein the strut has a length extending between the first and second ends along the direction and a width perpendicular to the length; and
    a first articular surface on the second end, wherein the first articular surface is shaped to replace a natural articular surface of the first vertebra;
    wherein the first articular surface is positioned on the strut independently of any other articular surface;
    wherein the strut width is narrower than the articular surface.

11. The system of claim 10, wherein the first articular surface is formed monolithically with the strut.

12. The system of claim 10, wherein the fixation member comprises a distal end configured to be retained in the pedicle independently of any threaded engagement.

13. The system of claim 10, wherein the first articular surface comprises an inferior articular surface.

14. The system of claim 10, wherein the first articular surface comprises a superior articular surface.

15. The system of claim 10, wherein the first prosthesis is configured to be securable to the first vertebra without resection of a lamina of the first vertebra, and without being supported by the lamina.

16. The system of claim 10, wherein the first prosthesis is configured to be securable to the first vertebra without requiring resection of any spinous process or transverse process of the first vertebra, and without requiring contact of the first prosthesis with any spinous process or transverse process of the first vertebra.

17. The system of claim 10, further comprising a second prosthesis securable to a second vertebra adjacent to the first vertebra, the second prosthesis comprising a second articular surface shaped to articulate with the first articular surface.

18. A method for replacing at least a portion of a natural facet of a first vertebra, the method comprising:
    implanting a fixation member of a first prosthesis in a pedicle of the first vertebra, the first prosthesis further comprising:
    a strut comprising a first end formed monolithically with the fixation member, and a second end extending from the first end along a direction transverse to a longitudinal axis of the fixation member, wherein the strut has a length extending between the first and second ends along the direction and a width perpendicular to the length, and
    a first articular surface on the second end; and
    positioning the first articular surface to replace a natural articular surface of the first vertebra;
    wherein the strut is shaped to avoid encircling a spinous process of the first vertebra;
    wherein the strut width is narrower than the articular surface.

19. The method of claim 18, wherein the first articular surface is positioned on the strut independently of any other articular surface.

20. The method of claim 18, wherein the first articular surface is formed monolithically with the strut.

21. The method of claim 18, wherein the fixation member comprises a distal end, the method further comprising retaining the distal end in the pedicle independently of any threaded engagement.

22. The method of claim 18, wherein the first articular surface comprises an inferior articular surface.

23. The method of claim 18, wherein the first articular surface comprises a superior articular surface.

24. The method of claim 18, further comprising securing the first prosthesis to the first vertebra without resecting a lamina of the first vertebra, and without supporting the first prosthesis with the lamina.

25. The method of claim 18, further comprising securing the first prosthesis to the first vertebra without resecting any spinous process or transverse process of the first vertebra, and without requiring contact of the first prosthesis with any spinous process or transverse process of the first vertebra.

* * * * *